United States Patent
Vaillant et al.

(10) Patent No.: US 7,113,631 B2
(45) Date of Patent: Sep. 26, 2006

(54) METHOD AND DEVICE FOR RECONSTRUCTION OF A DYNAMIC THREE-DIMENSIONAL IMAGE OF AN OBJECT COVERED BY A CONTRAST MEDIUM

(75) Inventors: Régis Vaillant, Villebon sur Yvette (FR); Dorothée Freymann, Strasbourg (FR); Laurent Launay, St. Remy les Chevreuse (FR); Erwan Kerrien, Versailles (FR)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 1082 days.

(21) Appl. No.: 09/920,586

(22) Filed: Aug. 1, 2001

(65) Prior Publication Data
US 2002/0123680 A1    Sep. 5, 2002

(30) Foreign Application Priority Data
Aug. 2, 2000 (FR) ................. 00 10211

(51) Int. Cl.
*G06K 9/00* (2006.01)
(52) U.S. Cl. ................ 382/154; 382/128
(58) Field of Classification Search ........ 382/128–134, 382/154, 274; 378/0.1–23; 600/419–420, 600/430–431
See application file for complete search history.

(56) References Cited
U.S. PATENT DOCUMENTS

| | | | |
|---|---|---|---|
| 5,241,471 A | * | 8/1993 | Trousset et al. ........... 382/274 |
| 5,287,273 A | * | 2/1994 | Kupfer et al. ............. 600/431 |
| 5,287,274 A | * | 2/1994 | Saint Felix et al. .......... 378/13 |
| 5,442,674 A | * | 8/1995 | Picard et al. ............... 378/20 |
| 5,827,187 A | | 10/1998 | Wang et al. ............... 600/419 |
| 6,073,042 A | * | 6/2000 | Simonetti ................. 600/420 |
| 6,510,241 B1 | * | 1/2003 | Vaillant et al. ............ 382/154 |
| 6,788,759 B1 | * | 9/2004 | Op De Beek et al. ........ 378/19 |

FOREIGN PATENT DOCUMENTS

| | | |
|---|---|---|
| FR | 8903606 | 9/1990 |
| FR | 8916906 | 6/1991 |
| FR | 9300804 | 9/1994 |
| FR | 9807371 | 12/1999 |
| WO | 9927382 | 6/1999 |
| WO | 0037957 | 6/2000 |

OTHER PUBLICATIONS

Chenevert et al, "Dynamic Three-Dimensional Imaging with Partial K-Space Sampling: Initial Application for Gadolinium-Enhanced Rate Characterization of Breast Lesions", Radiology 1995; 196:135-142.

* cited by examiner

*Primary Examiner*—Sherali Ishrat
(74) *Attorney, Agent, or Firm*—Cantor Colburn LLP

(57) ABSTRACT

The method comprises a phase of reconstruction of a static three-dimensional image of the object from a first set of digitized two-dimensional projected images of the object respectively obtained for different positions of a camera around the object, a phase of acquisition of at least a second set of n static two-dimensional projected images respectively obtained for a same first position of the camera and at n successive propagation times of the contrast medium, and a phase of reconstruction of the dynamic three-dimensional image of the object from each static two-dimensional image of the second set and the reconstructed static three-dimensional image.

21 Claims, 5 Drawing Sheets

METHOD AND DEVICE FOR RECONSTRUCTION OF A DYNAMIC THREE-DIMENSIONAL IMAGE OF AN OBJECT COVERED BY A CONTRAST MEDIUM

CROSS REFERENCE TO RELATED APPLICATIONS

This application claims the benefit of a priority under 35 USC 119 to French Patent Application No. 0010211 filed Aug. 2, 2000, the entire contents of which are incorporated by reference.

BACKGROUND OF THE INVENTION

The invention concerns the reconstruction of a three-dimensional image of an object covered by a contrast medium.

Its application is of particular interest in the medical field, in which reconstruction of the internal structures of patients under examination is undertaken and, in particular, the reconstruction of angiographic images, that is, obtaining images of opacified vasculatures by injection of a contrast medium.

The invention can, nevertheless, have applications in other fields, notably, in nondestructive industrial control, in which examinations of the same type as medical examinations are performed.

In the medical field, two-dimensional projected images of the object, for example, a patient's head, are generally obtained by rotation of an X-ray camera turning around the object. There are essentially two types of reconstruction algorithms in X-ray imaging. A first type provides for a calculation by back projection and filtering or even a Fourier transform reconstruction in several dimensions. A second type concerns the iterative methods of reconstruction, also called algebraic. The principle of such an algebraic algorithm is disclosed, for example, in French Patent Applications Nos. 8903606, 8916906 or 9807371, which describes an application of an iterative algorithm of algebraic reconstruction of images on a multi-resolution volume.

In short, after a calibration of the apparatus used to determine, notably, the parameters of projection in the projection planes of the acquired images, of an observed volume broken down into elementary volume elements or voxels (those calibration parameters forming projection matrices), the algebraic image reconstruction algorithm is used to reconstruct the three-dimensional volume from those two-dimensional projected images. The basic principle of that algorithm is to initialize the voxels of the volume to a predetermined initial value, for example, a zero value, and to iterate a number of times the following operations: projection of voxels in the plane of each acquired image so as to obtain a virtual image, determination of the difference between the projected volume (virtual image) and the corresponding acquired image, and then back projection of that difference in volume. After a number of iterations, an estimated value representative of the density of contrast medium injected in the vessels X-rayed is obtained for each voxel, which makes it possible to visualize in three dimensions the cartography of those X-rayed vessels.

Those three-dimensional images are of valuable assistance to the neurologist and the surgeon, whether for a diagnosis, planning of therapeutic procedures or evaluation of the shape and size of objects.

On the other hand, such reconstructed volume images have one major dis-advantage. Actually, they do not make it possible to visualize propagation of the contrast medium injected in the arteries, since the acquired two-dimensional images, from which the three-dimensional images has been reconstructed, are acquired for a quasi-stationary condition of the contrast medium. In fact, for the reconstruction of a three-dimensional image, which will be described here under the term "static" by reason of the quasi-stationary character of the contrast medium, it is sought rather to obtain a set of images corresponding to a same degree of propagation of the contrast medium.

Consequently, with such a reconstruction, the patient's vascular system cannot be analyzed with just three-dimensional information and blood flow information (propagation of contrast medium).

BRIEF DESCRIPTION OF THE INVENTION

An embodiment of the invention is directed to reconstruction of a three-dimensional image that will be described here as "dynamic," in contrast to the static three-dimensional image mentioned above, making it possible to visualize in three dimensions the propagation of the contrast medium in the object.

An embodiment of the invention is directed to a method of reconstruction of a dynamic three-dimensional image of an object covered by a contrast medium, the method comprising the steps of:

reconstruction (or reconstitution) of a static three-dimensional image of the object from a first set of digitized two-dimensional projected images of the object respectively obtained for different imaging positions around the object;

acquisition of at least a second set of n static two-dimensional projected images respectively obtained for a same imaging position and at n successive propagation times of the contrast medium, and reconstruction of the dynamic three-dimensional image of the object from each static two-dimensional image of the second set and the reconstructed (or reconstituted) static three-dimensional image.

The invention also proposes a device for reconstruction of a dynamic three-dimensional image of an object covered by a contrast medium, comprising:

first means for reconstructing a static three-dimensional image of the object from a first set of digitized two-dimensional projected images of the object, respectively obtained for different imaging positions around the object;

means for acquiring at least a second set of n static two-dimensional projected images from a same first position of the camera and corresponding to n successive propagation times of the contrast medium, and second means for reconstructing the dynamic three-dimensional image of the object from each static two-dimensional image of the second set and from the reconstructed static three-dimensional image.

The invention also concerns a device for reconstruction of a dynamic three-dimensional image of an object covered by a contrast medium, adapted for use of the method, as defined below.

The different means making possible the use of the method are software means executed by a microprocessor. The software means can be provided on a support, such as a read only memory and/or a diskette. The invention therefore also proposes a computer program comprising program code means employing the method, as defined below, when the program is executed in a processor.

The invention further proposes a support, such as a read only memory or a diskette, capable of being read by a processor, and containing program code means that can apply the method, when the program is executed in the processor.

BRIEF DESCRIPTION OF THE DRAWINGS

Other advantages and characteristics of the invention will appear on examination of the detailed description of non-limitative methods of use and embodiments and of the attached drawings, in which.

DETAILED DESCRIPTION OF THE INVENTION

According to one embodiment of the method, the latter comprises a calibration of the apparatus in which is elaborated a virtual volume surrounding the object and broken down into voxels. The reconstructed static three-dimensional image is then made up of estimates, called static estimates, respectively associated with the voxels of the virtual volume, each static estimate being representative for the corresponding voxel of the density of contrast medium injected in the object. The dynamic three-dimensional image is, in fact, composed of n elementary three-dimensional images corresponding to n propagation times of the contrast medium. A current elementary three-dimensional image corresponding to a current propagation time is reconstructed (1) from the static estimates of density of contrast medium injected in the object, (2) for each voxel, from the intensity of the pixel of the static two-dimensional image corresponding to the current propagation time, on which the voxel is projected, and (3) for each of those pixels, from the integral of the estimates of density of the voxels of the virtual volume situated along the line of sight associated with that pixel.

In some cases, several vessels can be projected on the same pixel. This generally corresponds to 10% of the voxels. It can result in ambiguity in estimation of the reconstructed dynamic three-dimensional image. Such ambiguity can be resolved by using another series of static two-dimensional images acquired from a vantage point different from that of the n two-dimensional images of the second set.

In other words, according to another embodiment, provision is made for a phase of acquisition of a third set of two-dimensional projected images respectively obtained for a same second position of the camera, separate from the first position (the one corresponding to acquisition of the two-dimensional projected images of the second set), and at the same successive propagation times of the contrast medium. The dynamic three-dimensional image of the object is then reconstructed from the reconstituted static three-dimensional image, from each image of the second set and from each image of the third set.

Although the invention is not limited thereto, the application of the method is described for the reconstruction of a dynamic three-dimensional angiographic image of a patient and, in particular, of the patient's head.

Figure 1:
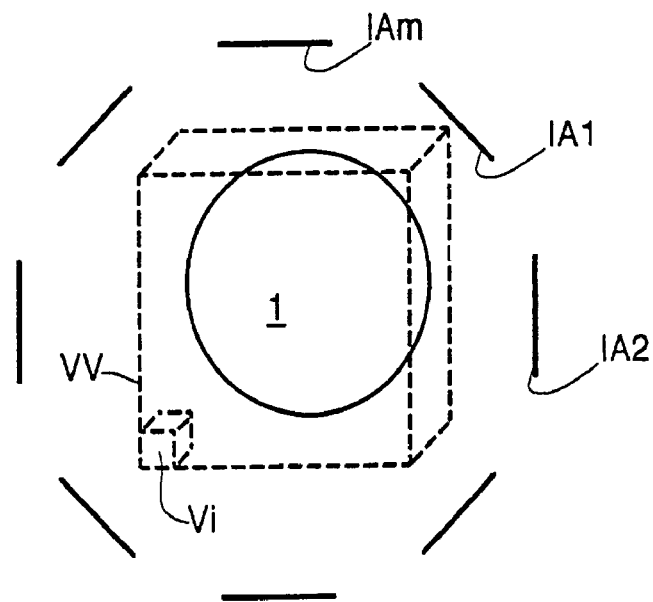
FIG. 1 schematically illustrates a set of two-dimensional projected images around an object.
Figure 2:
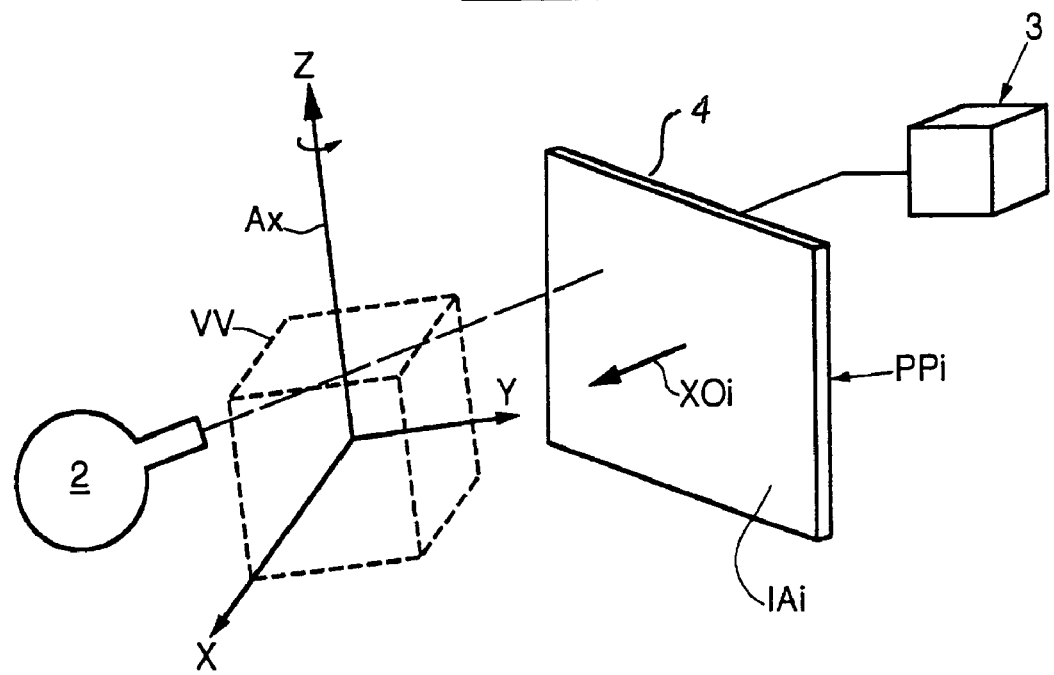
FIG. 2 illustrates in greater detail the acquisition of the two-dimensional projected images.

Referring, in particular, to FIGS. 1 and 2, the imaging system usable for applying the invention makes it possible to obtain, notably, a set of two-dimensional acquired images IA1-IAm obtained in this case by the rotation of an X-ray source 2 around a patient's head 1.

As is standard in angiography, each acquired image IAi is a subtracted image which is, for example, obtained by a standard technique of logarithmic subtraction of two X-rays taken at the same angle of incidence before and after an injection of a contrast medium in the vasculature, the three-dimensional image of which it is desired to reconstruct, first static and then dynamic as described.

More precisely, two sequences are acquired by rotation around the patient's head before and after injection of the contrast medium. In order to do so, the radiography apparatus, for example, makes two rotations of 193.5° in approximately 10 seconds, making possible the acquisition of 44 two-dimensional images taken every 4.5°. That acquisition of images IAi is intended for the three-dimensional reconstruction of an image of the vasculature, called static, that is, in which propagation of the contrast medium is not concerned. Under those conditions, that acquisition is made preferably when the contrast medium is quasi-stationary in the vessels studied.

Each acquired image IAi is obtained from a two-dimension radiation detector 4, for example, of the luminescence amplifier type used in radiology, placed opposite the X-ray tube in a plane called "projection plane PPi." The different projection planes are obtained by the different angular position of the detector in rotation around the patient's head.

The normal line XOi to the projection plane PPi defines the optical axis of the acquired image IAi. The detector is connected to processing means 3 containing, notably, sampling means connected to a microprocessor incorporating as software in its associated program memory the image reconstruction algorithm used in the invention and, in general, all of the functional means making possible the use of the method, such as the different image reconstruction means.

In the case of an X-ray imaging system, consisting of an X-ray source with two-dimensional detector, the geometric operation entering into production of the acquired image is a conical projection of an analyzed object, deployed in three-dimensional space, on a two-dimensional space which is that of the projection plane corresponding to the detection plane. The geometric parameters completely describing the different conical projections must be known. It is often impossible and too imprecise to access these parameters directly, that is, for example, by directly measuring on the system of acquisition the distance between the X-ray source and the detector.

The operation resulting in indirect knowledge of the geometric parameters entering into the production of an image is called "calibration" of an imaging system.

The principle, standard and known, is based on the use of a known geometric phantom in three-dimensional space, the two-dimensional projection of which is acquired. More precisely, calibration entails the following stages: (1) a known object is used, the calibration phantom, presenting a number of characteristic points whose position in space is known by coordinates measured in relation to a mark peculiar to that object; (2) the image of that phantom is acquired under the geometric conditions of a vantage point (or angle of incidence) that it is sought to calibrate; (3) the projections of the characteristic points are recognized in the image. For that purpose, each characteristic point of the object is joined to its trace in the acquired image projected; (4) the system of equation describing the projection is inverted; and (5) and the set of parameters of the projection is, finally, obtained for the given vantage point.

A form of geometric calibration phantom often used is that of a cube, with eight corners at which metal balls opaque to X-rays are placed. Calibration being an operation known to the expert, it will not be described more in detail.

A known method of automatic geometric calibration of an imaging system by X-rays can, nevertheless, be mentioned, such as that described in French Patent Application No. 9300804. In brief, a phantom is used for such automatic calibration, in which the balls are distributed from place to place in a sequence such as heights of balls, measured along the axis of rotation of the imaging system, and especially an axis of the phantom, or monotones increasing (or decreasing) with a serial number of balls in the sequence.

The calibration of the imaging system makes it possible, notably, to determine the estimated mean axis Ax of rotation of the camera around the object, as well as the position of the source 2 and the geometric characteristics of the optical axes of the different acquired images. Calibration also makes it possible to define a virtual volume VV (intersection of the different projection cones) surrounding the object 1 and broken down into elementary volume elements Vi or "voxels". That volume VV, and, therefore, each voxel Vi, is spatially marked in a reference system hereinafter called calibration reference system, one of the axes of which, in this case axis Z, is merged with the estimated axis of rotation Ax. It is to be noted here that the projection planes PPi in which the acquired images IAi are projected are not generally parallel to axis Z.

Calibration also enables a projection matrix Pi to be defined for each acquired image IAi, making it possible to determine, for each voxel Vi, the coordinates of its projection (pixel) in the corresponding acquired image IAi.

Figure 4:
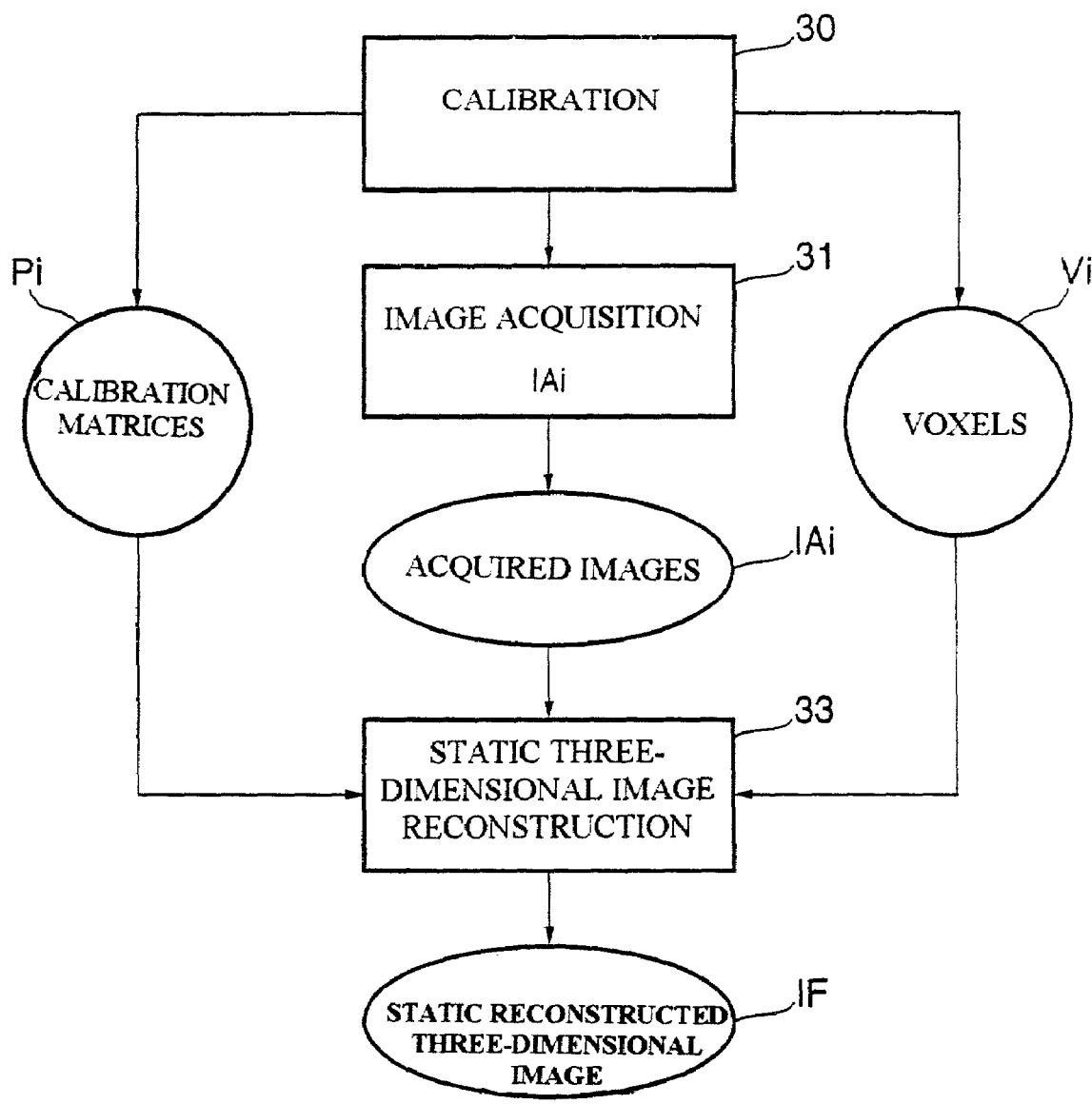
FIGS. 4 and 5 represent a flow chart of an embodiment of the method.

The phase of reconstruction of the three-dimensional image called "static" is now going to be described, with reference in particular to FIG. 4, from the first set of projected static two-dimensional images obtained IAi.

An algebraic image reconstruction algorithm is going to be applied directly on the images IAi (obtained after calibration 30 and acquisition 31), so as to deliver the reconstituted static three-dimensional image IF, typically after three iterations.

It is recalled that the basic principle of the image reconstruction algorithm used here consists of initializing the voxels of the volume at a predetermined initial value, for example, zero value, and then performing a number of iterations, typically three. Each iteration involves, for each acquired image, the projection of the voxel in the plane of each acquired image, so as to obtain a virtual image, determination of the difference between the projected volume (virtual image) and the corresponding acquired image, and then the back projection of that difference in the volume.

Generally, after three iterations, one obtains for each voxel of coordinates (ij,k), an estimate ci,j,k, designated here by the term static estimate, representative of the density of contrast medium injected in the vessels X-rayed, which makes it possible to visualize in three dimensions the cartography of those X-rayed vessels (image IF).

Of course, within the scope of this invention, it is not necessary to visualize the static three-dimensional image IF thus obtained on the display screen of the imaging system, since, in fact, it consists here only of an intermediate stage for obtaining, as is now going to be seen more in detail, the reconstructed dynamic three-dimensional image.

The expert may refer, if so desired, for more details concerning the use of such an algebraic algorithm of image reconstruction, to the aforementioned French Patent Application No. 9807371.

Figure 3:
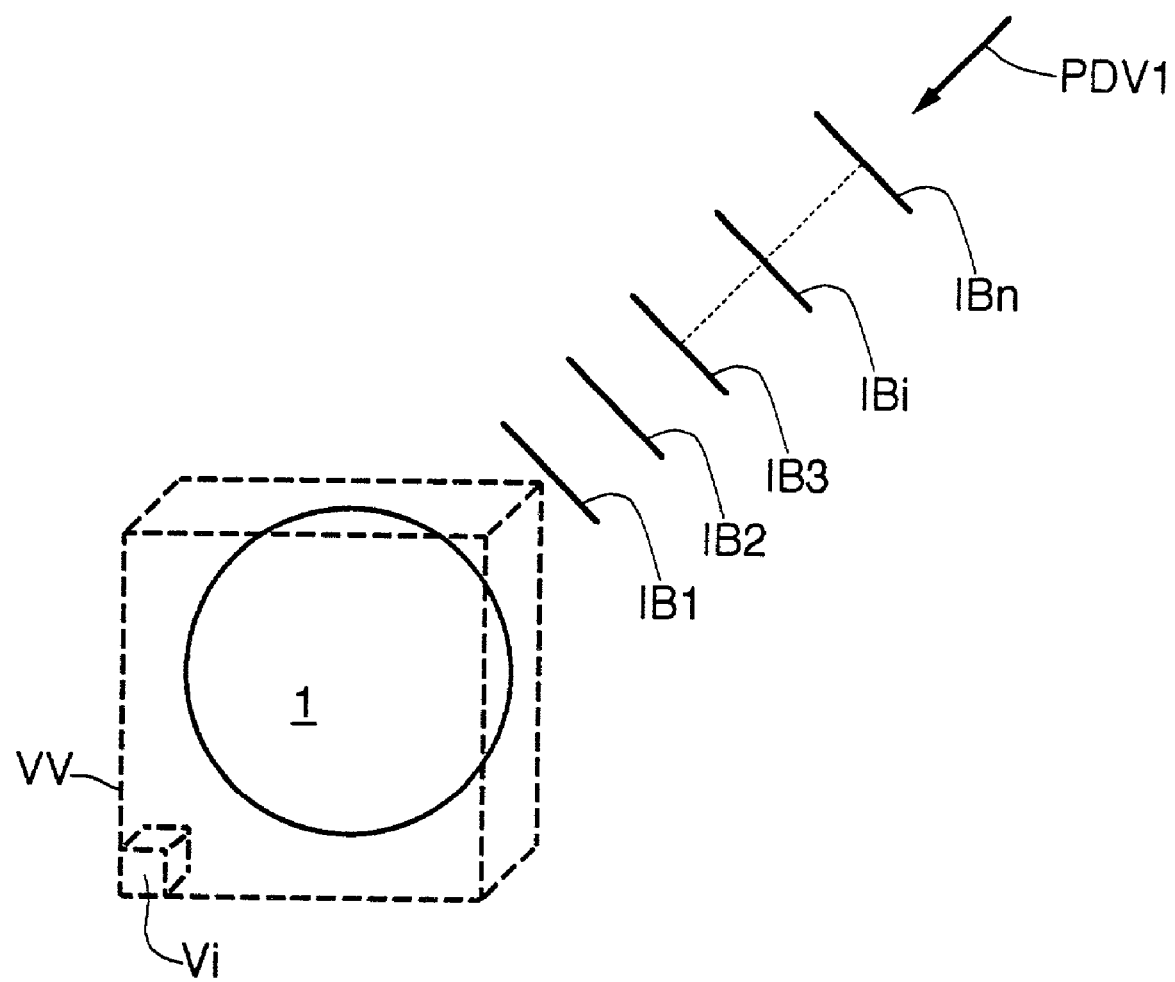
FIG. 3 schematically illustrates a set of projected static images acquired from a same vantage point.

In addition to acquisition of the first set of images IAi, the acquisition of a second set of static two-directional projected images IB1-IBn (FIG. 3) is undertaken. That series of images IBi is acquired for a same position of the camera, corresponding to a same vantage point PDV1.

The n images IBt thus acquired correspond to n successive propagation times of the contrast medium.

Figure 5:
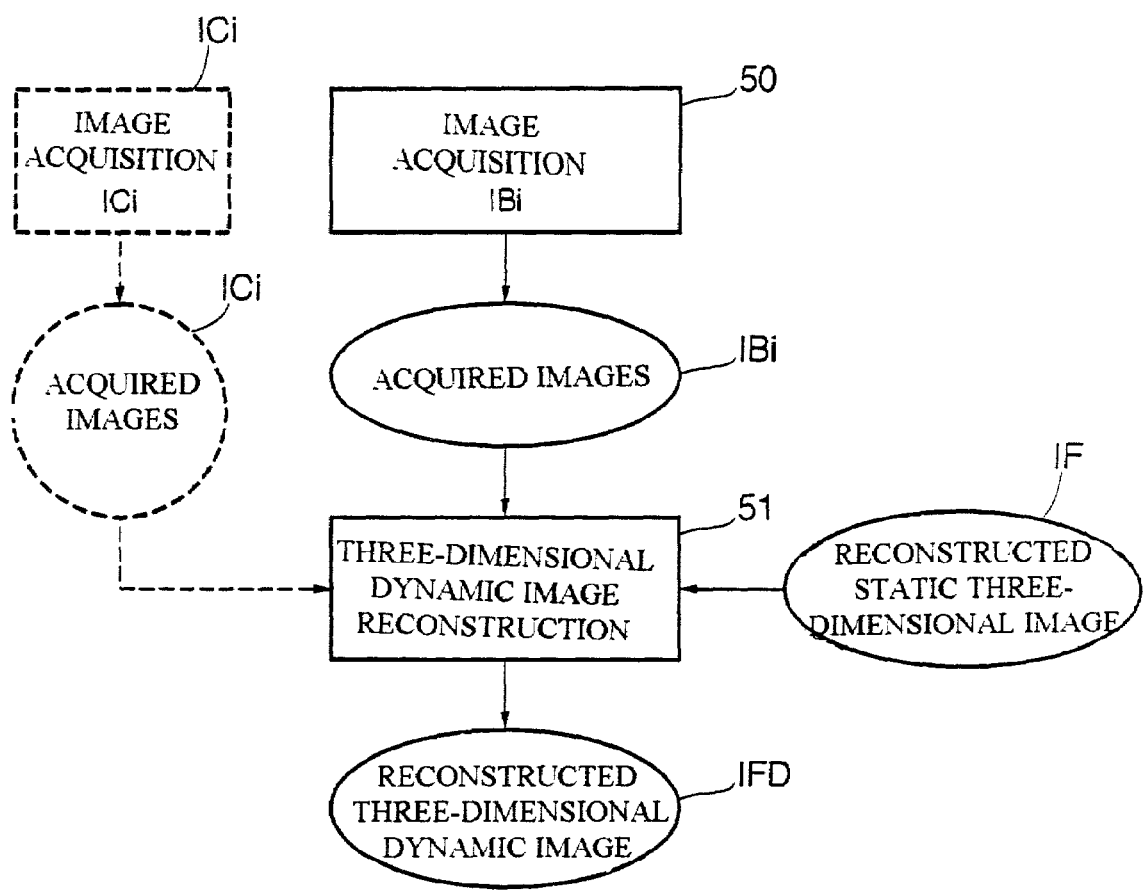

As illustrated in FIG. 5, from those images IBi acquired in the course of an acquisition stage 50, and from the reconstituted static three-dimensional image IF, the three-dimensional dynamic image of the vasculature is going to be reconstituted in a stage 51.

It is to be noted here that the order in which the acquisitions 31 (FIG. 4) and 50 (FIG. 5) are made after calibration does not matter for use of the method according to the invention.

The reconstituted three-dimensional dynamic image IFD is composed, in fact, of n elementary three-dimensional dynamic images, on each of which it is going to be possible to visualize the state of propagation at the given propagation time t of the contrast medium in the vasculature. By successively visualizing the n elementary three-dimensional images, it is going to be possible to visualize dynamically the propagation of the contrast medium in the vasculature.

Similar to what has been described above for the static reconstituted three-dimensional image, visualization of the dynamic reconstituted three-dimensional image is obtained by an estimate, for each value of coordinates (i, j, k) of the density of contrast medium at propagation time t. That estimate, valid at propagation time t, is designated by $c_{i,j,k}(t)$.

And that estimate is defined by formula (1) below:

$$C_{i,j,k}(t) = \frac{C_{i,j,k} \cdot p(t)}{E} \quad (1)$$

in which:

$c_{i,j,k}$ designates the static estimate of contrast medium of that same voxel in the static reconstituted three-dimensional image IF, p(t) designates the intensity of the pixel of the image IBt acquired at the propagation time t and on which the voxel of coordinates i,j,k is projected, and E designates for that pixel p the integral of the static estimates of density of the voxels of the virtual volume VV situated along the line of sight associated with that pixel p.

E is defined by formula (2) below:

$$E = \Sigma c_{ij,k} \, \lambda_{ij,k} \, i,j,k \quad (2)$$

in which $\lambda_{i,j,k}$ equals 0 if the voxel of coordinates i,j,k is not situated on the line of sight and equals 1 if it is situated on the line of sight.

It is to be noted here that determination of the pixel p is possible by reason of knowledge of the projection matrix associated with the series of static images taken along a predetermined line of sight. Likewise, the values λ in formula (2) are also known from the values of that projection matrix.

It is to be noted here that if at time t the voxel of coordinates i,j,k is not yet reached by the contrast medium, then there must be a low value for $c_{i,j,k}(t)$. If value p(t) is low, that is, if the density of the pixel projected is low, formula (1) is therefore going to well result in a low voxel density at time t.

On the other hand, if value p(t) is high, that means that the line of sight concerned crosses other luminous voxels which come to parasite the density due to the voxel of coordinates i,j,k concerned. Formula (1) then renders the voxel more accessible than it really is.

If the voxel of coordinates i,j,k is reached by the contrast medium, formula (1) can create artifacts, as in the preceding case, if the voxel considered is superposed with a voxel not yet reached by the contrast medium.

However, the above formula (1) makes possible a very good estimate of the dynamic reconstituted image, considering that the conditions of creation of artifacts mentioned above concern only approximately 10% of the voxels of the volume.

Figure 6:
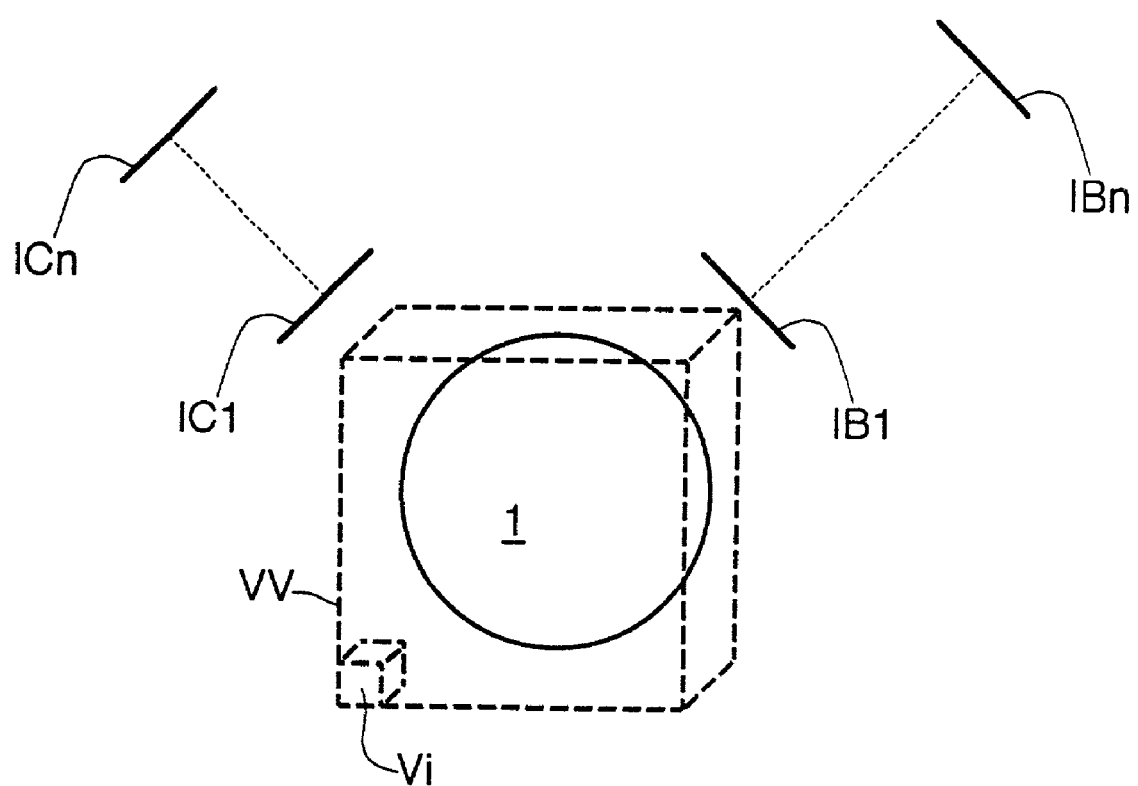
FIG. 6 schematically illustrates a variant embodiment of the invention.

Nevertheless, in order to resolve that ambiguity and consequently improve dynamic reconstruction of the image, one can, as mentioned in FIG. 6, undertake the acquisition of another series of n static two-dimensional images projected here from a vantage point different from the vantage point for the first series of images IBi. Images IBi ICi are respectively acquired at the same times.

In that case, as indicated in FIG. 5 in dotted lines, reconstitution of the three-dimensional dynamic image in stage 51 is also carried out from the images ICi acquired in stage 52.

A first value $c_{i,j,k}(t)$ will then be calculated for voxel i,j,k at time t, using images IBi, and a second value $c_{i,j,k}(t)$ will be calculated by this time using formula (1) in together with images ICi.

And the final value $c_{i,j,k}(t)$ associated with the voxel of coordinates i,j,k will then be equal to the lower of the two values mentioned above.

Various modifications in structure and/or steps and/or function may be made by one skilled in the art without departing from the scope and extent of the invention as recited in the claims.

What is claimed is:

1. A method of reconstruction of a dynamic three-dimensional image of an object covered by a contrast medium comprising:
   reconstruction of a static three-dimensional image of the object from a first set of digitized two-dimensional projected images of the object respectively obtained for different imaging positions around the object;
   acquisition of at least a second set of n static two-dimensional projected images respectively obtained for a same first imaging position and at n successive propagation times of the contrast medium; and
   reconstruction of the dynamic three-dimensional image of the object from each static two-dimensional image of the second set and the reconstructed static three-dimensional image.

2. The method according to claim 1 comprising
   calibration to elaborate a virtual volume surrounding the object and broken down into voxels, in that the reconstructed static three-dimensional image is then made up of static estimates, respectively associated with the voxels of the virtual volume, each static estimate being representative for the corresponding voxel of the density of contrast medium injected in the object, in that the dynamic three-dimensional image is composed of n elementary three-dimensional images corresponding to n propagation times of the contrast medium, and in that a current elementary three-dimensional image corresponding to a current propagation time is reconstructed;
   from the static estimates of density of contrast medium injected in the object;
   for each voxel from the intensity of the pixel of the static two-dimensional image corresponding to the current propagation time, on which the voxel is projected; and
   for each of those pixels, from the integral of the estimates of density of the voxels of the virtual volume situated along the line of sight associated with that pixel.

3. The method according to claim 1 comprising:
   acquisition of a third set of static two-dimensional projected images respectively obtained for a same second imaging position, separate from the first position, and at the same successive propagation times of the contrast medium, and in that the dynamic three-dimensional image of the object is reconstructed from the static three-dimensional image, from each image of the second set and from each image of the third set.

4. The method according to claim 2 comprising:
   acquisition of a third set of static two-dimensional projected images respectively obtained for a same second imaging position, separate from the first position, and at the same successive propagation times of the contrast medium, and in that the dynamic three-dimensional image of the object is reconstructed from the static three-dimensional image, from each image of the second set and from each image of the third set.

5. A device for reconstruction of a dynamic three-dimensional image of an object covered by a contrast medium, comprising
   first means for reconstructing a static three-dimensional image of the object from a first set of digitized two-dimensional projected images of the object, respectively obtained for different imaging positions around the object,
   means for acquiring at least a second set of n static two-dimensional projected images from a same first imaging position and corresponding to n successive propagation times of the contrast medium; and
   second means for reconstructing the dynamic three-dimensional image of the object from each static two-dimensional image of the second set and from the reconstructed static three-dimensional image.

6. The device according to claim 5 comprising:
   means for calibration to elaborate a virtual volume surrounding the object and broken down into voxels, in that the reconstructed static three-dimensional image is then made up of static estimates, respectively associated with the voxels of the virtual volume, each static estimate being representative for the corresponding voxel of the density of contrast medium injected in the object, in that the dynamic three-dimensional image is composed of n elementary three-dimensional images corresponding to n propagation times of the contrast medium, and in that a current elementary three-dimensional image corresponding to a current propagation time is reconstructed;
   from the static estimates of density of contrast medium injected in the object;
   for each voxel from the intensity of the pixel of the static two-dimensional image corresponding to the current propagation time, on which the voxel is projected; and
   for each of those pixels, from the integral of the estimates of density of the voxels of the virtual volume situated along the line of sight associated with that pixel.

7. A computer program embodied on a computer readable medium comprising program code means employing the method, as defined in claim 1, when the program is executed in a processor.

8. A computer program embodied on a computer readable medium comprising program code means employing the method, as defined in claim 2, when the program is executed in a processor.

9. A computer program embodied on a computer readable medium comprising program code means employing the method, as defined in claim 3, when the program is executed in a processor.

10. A computer readable medium, capable of being read by a processor, and containing program code means that can apply the method, as defined in claim 1, when the program is executed in the processor.

11. A computer readable medium, capable of being read by a processor, and containing program code means that can apply the method, as defined in claim 2, when the program is executed in the processor.

12. A computer readable medium, capable of being read by a processor, and containing program code means that can apply the method, as defined in claim 3, when the program is executed in the processor.

13. A computer readable medium, capable of being read by a processor, and containing program code means that can apply the method, as defined in claim 4, when the program is executed in the processor.

14. An article of manufacture for use with a computer system, the article of manufacture comprising a computer readable medium having computer readable program code means embodied in the medium, the program code means implementing the method according to claim 1.

15. An article of manufacture for use with a computer system, the article of manufacture comprising a computer readable medium having computer readable program code means embodied in the medium, the program code means implementing the method according to claim 2.

16. An article of manufacture for use with a computer system, the article of manufacture comprising a computer readable medium having computer readable program code means embodied in the medium, the program code means implementing the method according to claim 3.

17. An article of manufacture for use with a computer system, the article of manufacture comprising a computer readable medium having computer readable program code means embodied in the medium, the program code means implementing the method according to claim 4.

18. A program storage device readable by a computer tangibly embodying a program of instructions executable by the computer to perform the method according to claim 1.

19. A program storage device readable by a computer tangibly embodying a program of instructions executable by the computer to perform the method according to claim 2.

20. A program storage device readable by a computer tangibly embodying a program of instructions executable by the computer to perform the method according to claim 3.

21. A program storage device readable by a computer tangibly embodying a program of instructions executable by the computer to perform the method according to claim 4.

* * * * *

UNITED STATES PATENT AND TRADEMARK OFFICE
CERTIFICATE OF CORRECTION

PATENT NO.         : 7,113,631 B2                         Page 1 of 1
APPLICATION NO. : 09/920586
DATED               : September 26, 2006
INVENTOR(S)       : Vaillant et al.

It is certified that error appears in the above-identified patent and that said Letters Patent is hereby corrected as shown below:

Title Page,
Item (75), after "Villebon", delete "sur" and insert therefor --Sur--.
Item (75), after "St. Remy", delete "les" and insert therefor --Les--.

Title Page,
Primary Examiner, after "Sherali", delete "Sherali", and insert therefor --Sherali,--.

Column 5,
Line 57, after "coordinates", delete "(ij,k)," and insert therefor --(i,j,k),--.

Column 6,
Line 54, after "below", delete "E=Σcij,k λij,k i,,j,k" and insert therefor
--E=Σci,j,k λi,j,k i,,j,k--.

Signed and Sealed this

Twenty-seventh Day of February, 2007

JON W. DUDAS
*Director of the United States Patent and Trademark Office*